United States Patent
Bolondi et al.

(10) Patent No.: US 9,649,379 B2
(45) Date of Patent: May 16, 2017

(54) PHARMACEUTICAL COMPOSITION AND PHARMACEUTICAL KIT FOR THE TREATMENT OF HEPATOCELLULAR CARCINOMA

(75) Inventors: Luigi Bolondi, Bologna (IT); Catia Giovannini, Bologna (IT); Pásquale Chieco, San Lazzaro di Savena (IT); Kenneth Marcu, Stony Brook, NY (US)

(73) Assignee: ALMA MATER STUDIORUM—UNIVERSITA' DI BOLOGNA, Bologna (IT)

( * ) Notice: Subject to any disclaimer, the term of this patent is extended or adjusted under 35 U.S.C. 154(b) by 1597 days.

(21) Appl. No.: 12/452,825

(22) PCT Filed: Jul. 25, 2007

(86) PCT No.: PCT/IB2007/052957
§ 371 (c)(1),
(2), (4) Date: Mar. 17, 2010

(87) PCT Pub. No.: WO2009/013569
PCT Pub. Date: Jan. 29, 2009

(65) Prior Publication Data
US 2010/0189775 A1    Jul. 29, 2010

(51) Int. Cl.
*C12N 15/11* (2006.01)
*A01N 43/04* (2006.01)
*A61K 31/70* (2006.01)
*A61K 39/00* (2006.01)
*A61K 45/06* (2006.01)
*A61K 31/704* (2006.01)
*C12N 15/113* (2010.01)

(52) U.S. Cl.
CPC ............ *A61K 45/06* (2013.01); *A61K 31/704* (2013.01); *C12N 15/1138* (2013.01); *C12N 2310/111* (2013.01); *C12N 2310/14* (2013.01); *C12N 2310/53* (2013.01)

(58) Field of Classification Search
None
See application file for complete search history.

(56) References Cited

U.S. PATENT DOCUMENTS

2004/0102390 A1* 5/2004 Freier et al. .................... 514/44

FOREIGN PATENT DOCUMENTS

WO    00/20576    4/2000
WO    01/25422    4/2001

OTHER PUBLICATIONS

Abou-Alfa et al. J. Clin. Oncology, 2006 24(26) 2493-4300.*
Li et al. Gastroenterology, Jun. 2005 128(7) 2029-2041.*
Radtke et al. "The role of Notch in tumorigenesis: Oncogene or tumour suppressor?" Nature 3:756-767 Oct. 2003.
Roy et al. "The multifaceted role of Notch in cancer" Curr. Opn. Gen. Dev. 17:52-59 Feb. 2007.
Int'l Search Report for PCT/IB2007/052957, mailed Apr. 22, 2008.
Written Opinion for PCT/IB2007/052957, mailed Apr. 22, 2008.
Giovannini et al. "Characterization of Notch3 receptor in HEPG2 and HEP3B cell lines" Seventh International Conference of Anticancer Research, *Anticancer Research*, vol. 24, p. 3453, abstract 81 (Oct. 2004).
Giovannini et al. "Persistent Notch3 and Notch4 signaling in HEPG2 and HEP3B cell lines" 55th Annual Meeting of the American Association for the Study of Liver Diseases, *Hepatology*, vol. 40, No. 4, suppl. 1, p. 373A, abstract 481 (Oct. 2004).
Giovannini et al. "Notch3 intracellular domain accumulates in HepG2 cell line" *Anticancer Research*, vol. 26, No. 3A, pp. 2123-2127 (May 2006).
Gramantieri et al. "Expression of the components of the Notch signaling pathway in neoplastic and cirrhotic human liver" 39th Annual Meeting of the European Association for the Study of the Liver, *Journal of Hepatology*, vol. 40, suppl. 1, p. 103, abstract 340 (Apr. 2004).
Kim & Park "Molecularly targeted therapies for hepatocellular carcinoma: Sorafenib as a stepping stone" *Digestive Diseases*, vol. 29, pp. 303-309, abstract only (Sep. 2011).
Llovet et al. "Sorafenib in advanced hepatocellular carcinoma" *New England Journal of Medicine*, vol. 359, No. 4, pp. 378-390 (Jul 2008).

* cited by examiner

*Primary Examiner* — Doug Schultz
(74) *Attorney, Agent, or Firm* — Nixon & Vanderhye PC (57) ABSTRACT

The present invention provides pharmaceutical compositions for the treatment of hepatocellular carcinoma (HCC) comprising Notch3 inhibitors and a chemotherapeutic agent, methods for the preparation of said compositions and a medical treatment comprising the administration of said pharmaceutical compositions in patients in need thereof.

20 Claims, 4 Drawing Sheets

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: synthetic shRNA oligo#1 for Notch3

<400> SEQUENCE: 1
ctcccctcac cacctaataa a                                              21
```

```
<210> SEQ ID NO 2
<211> LENGTH: 24
<212> TYPE: DNA
<213> ORGANISM: Artificial Sequence
<220> FEATURE:
<223> OTHER INFORMATION: synthetic shRNA oligo#2 for Notch3

<400> SEQUENCE: 2
gggggacctg ccgccgtggc tata                                          24

<210> SEQ ID NO 3
<211> LENGTH: 20
<212> TYPE: DNA
<213> ORGANISM: Artificial Sequence
<220> FEATURE:
<223> OTHER INFORMATION: synthetic shRNA oligo#1 for Notch1

<400> SEQUENCE: 3
ggccgtcatc tccgacttca                                               20

<210> SEQ ID NO 4
<211> LENGTH: 19
<212> TYPE: DNA
<213> ORGANISM: Artificial Sequence
<220> FEATURE:
<223> OTHER INFORMATION: synthetic shRNA oligo#2 for Notch1

<400> SEQUENCE: 4
gcctcttcga cggctttga                                                19

<210> SEQ ID NO 5
<211> LENGTH: 20
<212> TYPE: DNA
<213> ORGANISM: Artificial Sequence
<220> FEATURE:
<223> OTHER INFORMATION: synthetic PCR forward primer for WAF1

<400> SEQUENCE: 5
aagaccatgt ggacctgtca                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic PCR reverse primer for WAF1

<400> SEQUENCE: 6
ggcttcctct tggagaagat                                               20

<210> SEQ ID NO 7
<211> LENGTH: 21
<212> TYPE: DNA
<213> ORGANISM: Artificial Sequence
<220> FEATURE:
<223> OTHER INFORMATION: synthetic PCR forward primer for P53

<400> SEQUENCE: 7
gacccaggtc cagatgaagc t                                             21

<210> SEQ ID NO 8
<211> LENGTH: 21
<212> TYPE: DNA
<213> ORGANISM: Artificial Sequence
<220> FEATURE:
<223> OTHER INFORMATION: synthetic PCR reverse primer for P53
```

```
<400> SEQUENCE: 8
accgtagctg ccctggtagg t                                              21

<210> SEQ ID NO 9
<211> LENGTH: 18
<212> TYPE: DNA
<213> ORGANISM: Artificial Sequence
<220> FEATURE:
<223> OTHER INFORMATION: synthetic PCR forward primer for HES1

<400> SEQUENCE: 9
gctggtgctg tctggatg                                                  18

<210> SEQ ID NO 10
<211> LENGTH: 19
<212> TYPE: DNA
<213> ORGANISM: Artificial Sequence
<220> FEATURE:
<223> OTHER INFORMATION: synthetic PCR reverse primer for HES1

<400> SEQUENCE: 10
cattcctgct ctcgccttc                                                 19
```

PHARMACEUTICAL COMPOSITION AND PHARMACEUTICAL KIT FOR THE TREATMENT OF HEPATOCELLULAR CARCINOMA

This is a U.S. national phase of Int'l Application No. PCT/IB2007/052957, filed 25 Jul. 2007, which designated the U.S.; the entire contents of which is hereby incorporated by reference.

FIELD OF THE INVENTION

The present invention provides pharmaceutical compositions for the treatment of hepatocellular carcinoma (HCC) comprising Notch3 inhibitors and a chemotherapeutic agent, methods for the preparation of said compositions and a medical treatment comprising the administration of said pharmaceutical compositions in patients in need thereof.

BACKGROUND OF THE INVENTION

Hepatocellular carcinoma (HCC) ranks fifth in frequency worldwide among all human cancer and causes 1 million deaths annually. Despite many promising treatment options, which include surgical resection, alcohol or radiofrequency ablation, chemoembolization, and liver transplantation, long-term prognosis remains poor in patients with advanced disease.

At present, embolization is the most widely used primary treatment for non-resectable HCC and has been the most-used therapy for patients awaiting liver donation for the prevention of HCC progression that might preclude transplantation. Embolization agents are usually administered together with selective intra-arterial cytotoxic agents, among them doxorubicin is most frequently used. Although this regimen significantly delays tumour progression and vascular invasion, this approach only achieves a partial response in patients.

Despite the recent development of new treatment modalities, the need to discover therapeutic molecules to overcome resistance to chemotherapeutic agents of HCC is still urgent. Notch receptors are implicated in proliferation, differentiation and apoptosis. Because of increasing evidence that the Notch signalling pathway is abnormally deregulated in human cancer, Notch receptors are potential targets for selective killing malignant cells.

The four known Notch receptors (Notch1-4) are single-pass transmembrane receptors that mediate signaling from the cell surface to the nucleus regulating proliferation, differentiation and apoptosis at all stages of development. Notch receptors are mainly activated by trans-membrane ligands of the Delta and Serrate/jagged families, which are expressed on the surface of neighboring cells. Ligand-mediated activation of Notch induces the proteolytic cleavage and nuclear translocation of a Notch intracellular domain (NICD) that binds to the transcription factor CBF1/RBP-Jk to trans-activate target genes, including HES1.

Deregulated Notch receptor expression has been reported in a variety of different human tumors. Increased Notch1 protein expression has been observed in human cancers of the breast, pancreas and also in Hodgkin lymphoma. Overexpression of Notch3 and Notch4 proteins has been detected in malignant melanoma, pancreatic cancer and breast cancer.

The Notch1 signaling pathway is activated during rat liver regeneration and over-expression of Notch1 has been found to inhibit the growth of HCC cells in vitro and in vivo.

It appears that constitutive activation of Notch1 may function as a tumor suppressor in small cell lung cancer cells, in prostate cancer cells and in mouse skin by inducing cell growth arrest.

Notch3 has been recently found to be highly expressed in the Human HepG2 liver carcinoma cell line; but up to now there are no studies concerning Notch3 functions in HCC.

In the field of tumors, gene therapy represents a new and promising strategy that relies on the transfer of genetic material into cells to produce a beneficial effect against the disease. Small interfering RNA (siRNA) is an emerging technology that capitalizes on a natural property of all cells to direct the silencing of specific genes by promoting either the degradation or ablating the translation of target mRNAs. Over the past several years a variety of vehicles have been developed to express and deliver short hairpin RNAs (shRNAs), which are efficiently converted into siRNAs by the natural RNA processing machinery of mammalian cells. Thus because of the established high specificity for their target mRNAs, specific shRNAs are being examined for the development of potential new therapies against a variety of human diseases including cancer.

Although it is known that Notch receptors, depending on their levels of expressions in various cellular contexts play a key role in the apoptotic resistance of malignant cells, their mechanism of action remains largely unknown, thus limiting the possibility of medical treatments against tumors related to said receptors.

Concerning the HCC, the medical limits against said disease listed above, underline the need, in the medical field, of drugs providing an effective treatment against the spreading and the survival of the HCC malignant cells.

SUMMARY OF THE INVENTION

In the present invention, the expression of Notch receptors in human tissue samples of HCC and adjacent HCC-free tissue has been explored; and the physiological effects of ablating Notch3 expression by shRNA in HepG2 cells have been assessed. It has been found that Notch3 is selectively expressed in HCC but not in surrounding HCC-free tissue.

Figure 6:
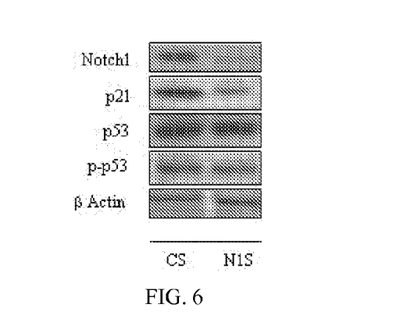

Consistent with a previous study on HCC cell lines that showed that Notch1 over-expression inhibits cellular growth through p21 up regulation, the authors of the present invention found that loss of Notch1 expression by targeted shRNA knock-down greatly reduced p21 protein expression by immunoblot analysis (FIG. 6).

However, contrary to what would be expected based on prior art and other results obtained for the Notch1 receptor in HCC, it was surprisingly found that inhibition of Notch3 activity by targeted shRNA or by anti-Notch3 antibodies, did not alter HepG2 growth rates. In this context, cell growth parameters were assessed one week post-infection by propidium iodide staining in conjunction with flow cytometry. The results obtained showed that Notch3 knock-down in HepG2 cells caused the accumulation of phosphorylated p53 and repression of p21 with no apparent effect on cellular growth or viability. Thus contrary to Notch1, Notch3 does not appear to contribute to the proliferation of human HCC, at least in this in vitro context.

Figure 3:
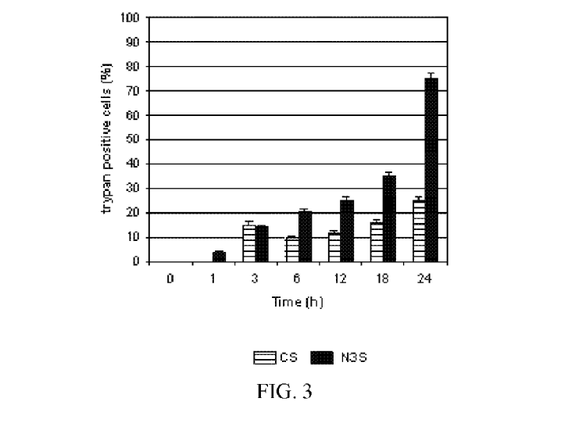

Remarkably, the mortality of HepG2 cells stably expressing Notch3 shRNAs (in comparison to a luciferase shRNA negative control) doubled and tripled in response to doxorubicin (or other molecules used for cancer therapy) treatments of 6 and 24 hours respectively, as revealed by trypan blue dye exclusion (FIG. 3).

Figure 10:
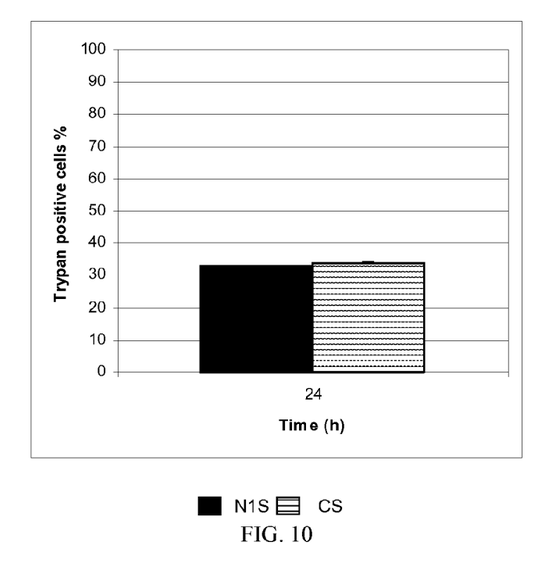
FIG. 10 Post doxorubicin treatment cell viability in Notch1 depleted cells $250 \times 10^3$ Infected cells were treated with 100 μg/ml of doxorubicin for 24 h Trypan viability was reproduced twice after each doxorubicin treatment, counting at least 200 cells per sample. Columns average of two independent experiments; bars, SE. CS: control shRNA, N1S; Notch1 shRNA.

On the other hand, Notch1 ablation had no demonstrable effect on their drug induced apoptosis as shown in FIG. 10.

Notch3 expression, hence, functions at least in part as a specific positive effector of multi-drug resistance by preventing the activation of p53-dependent apoptosis and, as a consequence, engenders HCC with resistance to chemotherapeutics or other environmental stresses.

Hence, objects of the invention are: a pharmaceutical composition comprising a Notch3 inhibitor, an anti-tumoral chemotherapeutic agent and pharmaceutical acceptable carriers, for the treatment of Hepatocellular Carcinoma, the method for the preparation of the said composition and a medical treatment comprising the administration of said compositions to patients in need thereof.

DETAILED DESCRIPTION OF THE FIGURES

FIG. 1. Increased Notch3 immunoreactivity in HCC relative to adjacent HCC-free liver tissue. Formalin fixed paraffin embedded section of HCC and surrounding tumor-free liver were immunostained with Anti-Notch3 polyclonal antibody. Immunoreactivity was revealed with a HRP rabbit EnVision system, and diaminobenzidine as the chromogen (brown precipitate). Sections were counterstained with Mayer's hematoxylin. The pictures are representative examples of HCC (A,C) and surrounding HCC-free liver (B,D) immunostained with a polyclonal antibody to Notch3.

FIG. 2. Protein and gene expression. (A) Western blots of Notch3, p53, p-p53, p21, Gadd45α, p27 in HepG2 infected cells. Densitometric analysis showed a 5-fold reduction in p21 levels and an increased protein expression of p27 (2.3-fold), Gadd45 (2-fold), p53 (5-fold) and p-p53 (3.2 fold) in Notch3 depleted cells. β Actin was used as a reference control for both mRNA and protein levels. (B) Western blots showing that both Notch3 shRNAs produced equally penetrant Notch3 knock-downs. (C) RT-PCR expression analysis of HES1, p53 and WAF in shRNA expressing HepG2 cells. Two independent experiments were carried out. CS: GL2 negative control shRNA, N3S: Notch3 shRNA.

FIG. 3. Post treatment cell viability. Infected cells were treated with 100 μg/ml of doxorubicin for the indicated times. Trypan viability was reproduced twice after each doxorubicin treatment, counting at least 200 cells per sample. Columns average of two independent experiments; bars, SE. CS: GL2 negative control shRNA, N3S: Notch3 shRNA.

FIG. 4. Apoptosis analysis. Cultured infected HepG2 cells were treated with 100 μg/ml of doxorubicin for 6 h, 12 h, 18 h and 24 h followed by protein extraction. Proteins were resolved by polyacrylamide gel electrophoresis followed by western blot analysis with monoclonal anti-Human Cleaved PARP. β Actin served as a protein level reference control. CS: GL2 negative control shRNA, N3S: Notch3 shRNA.

FIG. 5. Analysis of DNA damage and doxorubicin uptake. (A): DNA damage detected by the comet assay. Infected HepG2 cells were cultured in complete medium with 100 μg/ml doxorubicin for 1 h, 3 h, 6 h, 12 h, 18 h; and DNA strand breakage was subsequently measured by the comet assay. Basal DNA damage (without doxorubicin) showed that negative control HepG2 cells had the same damage of Notch3 depleted cells (P=0.6686). (B): Doxorubicin uptake. Infected cells were treated, for different times with 100 μg/ml of doxorubicin and drug uptake was determined by FACS analysis. Notch3 depleted cells took up significantly higher levels of doxorubicin than the negative control. Columns are the average of two independent experiments; bars, SE. CS: control shRNA, N3S; Notch3 shRNA FIG. 6. Decreased p21 expression in Notch1 depleted cells. Western blot analyses demonstrating decreased levels of p21 and unchanged levels of both p53 and p-p53 in Notch1 depleted cells (N1S) compared with negative control (CS).

FIG. 7. p53 short interference RNA. Infected cells were transfected with 40 nM of p53 siRNA or with 40 nM of scrambled siRNA (scRNA) and p53 knock-down was evaluated 48 h and 72 h post-transfection by western blotting. N3S: Notch3 shRNA; CS: GL2 negative control shRNA; scRNA: scrambled RNA. 1,7: N3S/scRNA; 2,8: CS/scRNA; 3,5: N3S/p53 siRNA; 4,6: CS/p53 siRNA.

FIG. 8. p53 siRNA decreases the sensitivity to doxorubicin in Notch3 depleted cells. Forty-eight and seventy-two hours post-transfection cells were treated with 100 μg/ml of doxorubicin for 24 h. Trypan viability was reproduced twice after each doxorubicin treatment, counting at least 200 cells per sample. Columns average of two independent experiments; bars, SE. CS: GL2 negative control shRNA, N3S; Notch3 shRNA; scRNA: scrambled RNA.

FIG. 9. HES1 short interference RNA. HepG2 cells were transfected with 40 nM of HES1 siRNA or with 40 nM of scrambled RNA and HES1 knock-down and p21 protein levels were evaluated 72 h post-transfection by RT-PCR and western blot respectively. 1: scrambled RNA, 2,3: different HES1 siRNA.

DETAILED DESCRIPTION OF THE INVENTION

According to the present invention Notch3 inhibition can be induced at the post-transcriptional level by targeted siRNAs or shRNAs or targeted synthetic oligonucleotides that hybridize with Notch3 mRNA (i.e. by RNA interference, RNAi), thus inhibiting the synthesis of Notch3 receptors.

Short hairpin RNA (shRNA) is an RNA molecule in the form of a stable hairpin which silences gene expression via RNA interference in vivo.

The shRNA hairpin structure is cleaved by cellular processing machinery to produce the mature siRNA, whose anti-sense strand is specifically taken up by the RNA-induced silencing complex (RISC). The latter complex binds to and cleaves mRNAs which match the siRNA sequence contained in the RISC, thus guiding the targeted RNA to degradation. Hence, the said inhibition will result in a certain time, in the depletion of Notch3 receptors from the target cells as the pre-existing receptors will eventually turn over but will not be replenished aced by newly synthesized Notch 3 receptors.

Alternatively, the receptors can be inhibited by using anti-Notch3 antibodies or molecules interfering with the functionality of the Notch3 receptor such as, by way of example, antagonists of the ligand of the receptor.

The shRNAs or siRNAs according to the invention can be constructed starting from the known mRNA sequence of Notch3, or selected among the ones described in the PCT application WO2004047731, or can be the ones of SEQ ID 1 and 2.

These RNAs are generally 21-23 nucleotides in length as it has been reported in the art that sequences longer than 30 nucleotides can elicit an anti-viral like interferon response that can results in the cessation of all protein synthesis.

Protocols and services for designing siRNAs or shRNAs are available online (by way of example genelink dot com slash sirna slash shRNAi dot asp and ambion dot com slash techlib slash misc slash psilencer converter dot html). Thus a skilled person would have no problems to design RNAs suitable for carrying out this invention.

The said shRNAs can be inserted in any vector suitable for gene therapy. shRNA expression vectors have been engineered using both viral (including retroviral, adenoviral and lentiviral vectors), and plasmid systems. These vectors utilize promoters from a small class of pol. III promoters to drive the expression of shRNA. All vectors have to include a promoter for human Pol III. The Human U6 promoter is the best studied type III pol promoter frequently used in RNAi.

shRNAs are exported from the nucleus by Exportin 5, which recognizes short RNA loop. Once in the cytoplasm, both pre-miRNAs and shRNAs are processed into siRNA duplexes by cleavage with a second RNase III enzyme termed Dicer. Importantly, Dicer binds the base of the shRNA and cleaves 21 or 22 nt up the stem, leaving a second 2 nt 3' overhang and forming an siRNA duplex structure. RNA duplex is taken up by the RNAi-Induced Silencing Complex (RISC). RISC unwinds the double-strand RNA and the activated complex with the associated antisense.

The genetic material in retroviruses is in the form of RNA molecules, while the genetic material of their hosts is in the form of DNA. When a retrovirus infects a host cell, it will introduce its RNA together with some enzymes into the cell. This RNA molecule from the retrovirus must produce a DNA copy from its RNA molecule before it can be considered as part of the genetic material of the host cell. The process of producing a DNA copy from an RNA molecule is termed reverse transcription. It is carried out by one of the enzymes carried in the virus, called reverse transcriptase. After this DNA copy is produced and is free in the nucleus of the host cell, it must be incorporated into the genome of the host cell by using another enzyme carried in the virus called integrase. One of the problems of gene therapy using retroviruses is that the integrase enzyme can insert the genetic material of the virus in any arbitrary position in the host's genome. If genetic material happens to be inserted in the middle of one of the original genes of the host cell, this gene will be disrupted (insertional mutagenesis). If the gene happens to be one regulating cell division, uncontrolled cell division (i.e., cancer) can occur. The state of the art in this field has disclosed the use of retroviral vectors utilizing zinc finger nucleases or including certain sequences such as the beta-globin locus control region to direct the site of integration to specific chromosomal sites The skilled person would know, however, where to find indications in the state of the art for the construction of a vector suitable for the pharmaceutical composition of the invention. Vectors, kit construction vectors and services for the construction of vectors for the expression and the targeting of said RNAs are known in the art, such as, by way of example, the INGENEX GeneSuppressorRetro Construction Kit, or are available online, or are described in the art in: Arts, G. J. et al. (2003) "*Adenoviral vectors expressing siRNAs for discovery and validation of gene function*". *Genome Res.* 13: 2325-2332. that demonstrates adenovirus-based shRNA expression in a variety of cell types, including primary cells; Matta, H. et al. (2003). "*Use of lentiviral vectors for delivery of small interfering RNA*". *Cancer Biol. Ther.* 2: 206-210. wherein the authors use Invitrogen's pLenti6 backbone to express an shRNA cassette; Tiscornia, G. et al. (2003). "*A general method for gene knockdown in mice by using lentiviral vectors expressing small interfering RNA*". *Proc. Natl. Acad. Sci. USA* 100: 1844-1848. that demonstrates the utility of lentiviral vectors for delivery of shRNA to cells and mice.

Advantageously, the vector of the invention could comprise a tumour specific promoter driving shRNA or siRNA expression in cells only in the tumour, or could instead comprise a liver specific promoter known in the art, such as, by way of example albumin, alpha 1-antitrypsin, human insulin-like growth factor II. An exhaustive list of liver specific promoters can also be found on the Liver Specific Promoters Database rulai dot cshl dot edu slash LSPD) in order to allow the skilled person to drive the expression of the retroviral vector and hence of the Notch3 inhibitor, only in the liver. This embodiment would be very advantageous as Notch3 has been proven herein to be expressed only in HCC cells and not in healthy or even cirrhotic liver cells. Hence, the inhibition of Notch3 according to the present invention would not cause unwanted molecular alterations in the HCC-free hepatocytes surrounding neoplastic nodules. This is of particular relevance because of the high prevalence of liver cirrhosis in hepatocellular carcinoma patients. The pharmaceutical composition of the present invention would hence allow targeted anti-cancer therapies that can be coupled with strategies aimed at reversing the progression of chronic liver disease in order to achieve long-term survival of the majority of patients.

The advantage of the pharmaceutical composition of the invention comprising such a vector lies in the fact that it would multiply the apoptotic effect of the chemotherapeutic drug only in the tumour, thus sensibly decreasing the negative effect of the drug on the surrounding healthy or even suffering but not neoplastic cells.

The same applies when the Notch3 inhibitor of the invention is represented by an Anti-Notch3 antibody or by any other embodiment herein described.

In general, the pharmaceutical composition of the invention is extremely advantageous, as the drug dose that is currently in use could be reduced due to the enhancement of its effect only in the malignant cells expressing Notch3. Synthetic oligonucleotides are useful for research in molecular biology, for clinical diagnosis and for the development of new therapeutic agents. In fact, their application to gene therapy has given rise to a new field termed anti-sense, enabling the synthesis of a new generation of drugs. The procedure is based on coupling an oligonucleotide with mRNA to yield the protein whose production by the host is to be prevented, and thus through diverse pathways inhibiting gene expression. In medicine, a start has been made by applying anti-sense techniques in human drug trials, particularly as anti-viral and anti-leukemic agents.

Hence, as an alternative to the RNA interference, Notch3 can be inhibited also by using synthetic oligonucleotides. Such synthetic oligonucleotides could be loaded into lipoplexes and that would be delivered directly into the liver by portal vein injection.

In an embodiment of the invention, the delivery of the synthetic oligonucleotides of the invention into the cell, is achieved by the construction of lipoplexes or polyplexes, as they have the ability to protect the oligonucleotides from undesirable degradation during the transfection process.

The oligonucleotides, can be covered with lipids in an organized structure like a micelle or a liposome. When the organized structure is complexed with the nucleic acid it is called a lipoplex. There are three types of lipids, anionic (negatively charged), neutral, or cationic (positively charged). Initially, anionic and neutral lipids were used for the construction of lipoplexes for synthetic vectors. Cationic lipids, due to their positive charge, naturally complex with the negatively charged nucleic acids and they are also less time consuming to produce than anionic of neutral lipids. Moreover due to their positive charge they also interact with the cell membrane facilitating their endocytosis and subsequent release of the nucleic acid into the cytoplasm. The cationic lipids also protect against degradation of the nucleic acid by the cell.

The skilled person would easily find in the art the protocols for the realization of the lipolexes of the invention.

The most common use of lipoplexes has been in gene transfer into cancer cells, where the supplied genes have activated tumor suppressor control genes in the cell and decrease the activity of oncogenes. Recent studies have shown lipoplexes to be useful in transfecting respiratory epithelial cells, so they may be used for treatment of genetic respiratory diseases such as cystic fibrosis.

In another embodiment of the invention, the Notch3 inhibition can be achieved by using, as inhibitor, such as an anti-Notch3 antibody, or a Notch3 receptor antagonist or any other molecule capable of blocking the functionality of the Notch3 receptor.

According to the present invention, the anti-tumoral chemotherapeutic agent can be selected among any suitable known chemotherapeutic agent causing apoptosis of the cell or acting on cellular proliferation among those, but not limited to them, the chemotherapeutical agent may be selected in the group comprising Doxorubicin, 5 Fluorouracil, Paclitaxel, Irinotecan, Patupilone, Everolimus, multikinase inhibitors (Sorafenib and Sunitinib), EGFR inhibitors (Cetuximab, Erlotinib, Gefitinb, Brivanib, Lapatinib). The pharmaceutical composition of the invention may be prepared in a form suitable for intravenous or intra-tissue injection and the preparation of it will comprise the steps of admixing the Notch3 inhibitor with one or more of the anti-tumoral drugs as defined in the present description and pharmaceutically acceptable carriers.

Alternatively, the two active compounds may be co-administered starting from 2 separate vials, either simultaneously or, when the inhibitor acts through post transcriptional inhibition of the Notch3 mRNA, the inhibitor can be administered 6 to 48 before the anti-tumoral chemotherapeutical agent.

Hence, the object of the invention is also a pharmaceutical kit for the co-administration of a Notch3 inhibitor, an anti-tumoral chemotherapeutic agent and pharmaceutical acceptable carriers, for the treatment of Hepatocellular Carcinoma comprising two vials, wherein one vial contains a Notch3 inhibitor and pharmaceutically acceptable carriers, and the other vial contains an anti-tumoral chemotherapeutic agent and pharmaceutically acceptable carriers.

According to the invention, the vial comprising the Notch3 inhibitor comprises a Notch 3 inhibitor selected among the group comprising siRNAs complementary to the mRNA coding for Notch3, shRNAs complementary to the mRNA coding for Notch3, synthetic oligonucleotides complementary to the mRNA coding for Notch3 or anti-Notch3 antibodies or Notch3 antagonists. The said siRNAs or shRNAs will be inserted in a viral vector according to the invention whereas the synthetic oligonucleotides will be combined with suitable lipids into lipoplexes The vial comprising the chemotherapeutic agent will comprise a chemotherapeutic agent selected in the group comprising Doxorubicin, 5 Fluorouracil, Paclitaxel, Irinotecan, Patupilone, Everolimus, multikinase inhibitors (such as, by way of example, Sorafenib and Sunitinib), EGFR inhibitors (such as, by way of example, Cetuximab, Erlotinib, Gefitinb, Brivanib, Lapatinib). In general, when the composition will comprise RNA Notch3 inhibitors, said RNA will be inserted in a suitable viral vector as indicated above.

Hence, the pharmaceutical composition of the invention will comprise the above mentioned vectors and one or more anti-tumoral agent as indicated in the present description.

When the inhibition will be performed by the oligonucleotides of the invention, said oligonucleotides will be complexed into lipoplexes, said lipoplexes will be suspended in a pharmaceutically acceptable solution suitable for intravenous injection together with one or more anti-tumoral chemotherapeutical agent (Doxorubicin, 5 Fluorouracil, Paclitaxel, Irinotecan, Patupilone, Everolimus, Sorafenib, Sunitinib, Cetuximab, Erlotinib, Gefitinb, Brivanib, Lapatinib)

In case of anti-Notch3 antibodies the antibodies will be suspended in a pharmaceutically acceptable solution suitable for intravenous injection together with one or more of the said anti-tumoral agent.

The same applies when a Notch3 antagonist or any other molecule capable of blocking Notch3 function is used as a Notch3 inhibitor.

The doses of the anti-tumoral chemotherapeutic component of the invention could be reduced 2-3 fold, due to the 2-3 fold enhancement of the effect of said drugs in the context of Notch3 suppression.

The pharmaceutical composition of the invention can advantageously comprise further compounds for the treatment of other liver diseases that may be present in combination with the HCC, such as compounds for the treatment of liver chirrosis and others.

The method for the preparation of the composition of the invention will hence comprise the steps of a. selecting a functional Notch3 inhibitor, said inhibitor being characterized by the fact that it inhibits either the synthesis of the Notch3 receptor or the functionality of the Notch3 receptor, b. admixing the inhibitor selected in a. with one or more anti-tumoral chemotherapeutic agent and pharmaceutically acceptable carriers.

When the inhibitor will be an RNA said RNA will be inserted in a suitable vector as previously indicated in order to allow the expression of said RNA in liver cells.

The invention also comprises a method for the preparation of the kit above described comprising the steps of:

a. preparing a first vial comprising a Notch3 inhibitor and pharmaceutically acceptable carriers;

b. preparing a second vial comprising one or more anti-tumoral chemotherapeutic agent and pharmaceutically acceptable carriers.

The inhibitors and the chemotherapeutical agents will be the ones described in the present specification.

Object of the invention is also a medical treatment of HCC comprising administering the pharmaceutical composition as described above to patients in need thereof, in therapeutically effective doses or co-administering the content of the vials of the pharmaceutical kit of the invention wherein the second vial may be administered in concomitantly or within 6 to 48 hours from the administration of the first vial.

In an advantageous embodiment of the invention, the medical treatment will be carried out by injecting the pharmaceutical composition of the invention or the first and second vial of the kit of the invention into the portal vein in order to be directly delivered to the liver.

The HCC treatment of the invention can also be advantageously combined with treatments for hepatic cirrhosis as above explained.

EXAMPLES

1. Patients and Methods

Twenty patients (12 men and 8 women) undergoing surgery for HCC entered the study. Informed consent was obtained from each patient according to the guidelines of the NIH and the latest version of the Helsinki Declaration. All patient identifiers were also removed from all tissue samples prior to analysis. Tissue samples were fixed in 10% formalin and paraffin-embedded for histopathological examination and immunohistochemistry. Cirrhosis (CE) was present in 13 out of 20 cases; the remaining cases displaying normal liver (2 cases) or chronic active hepatitis (CAH, 5 cases). The aetiology of the chronic liver disease was ascribed to HCV in 9 cases, HBV in 5 cases, HBV and HCV co-infection in 4 cases. No viral marker was recognized in two cases of HCC which developed from otherwise normal liver. Histopathological grading of HCCs was scored according to Edmonson and Steiner's criteria (31). One case was assessed as G1, 5 cases as G2, 12 cases as G3 and the remaining 2 cases as G4.

2. Immunohistochemistry

Formalin-fixed, paraffin embedded sections (4 µm thick) of HCC and adjacent tumor free liver were immunostained to detect Notch receptors. Primary antibodies recognizing Notch3 and 4 were
obtained from Santa Cruz Biotechnology (Santa Cruz, Calif.), whereas primary antibody for Notch1 was obtained from Abcam (Ab8925). Dilutions of the primary polyclonal antibodies were as follows: Notch1 (1:600), Notch3 (1:300) and Notch4 (1:400). Immunoreactivity was revealed with the HRP (Horse-Radish-Peroxidase) rabbit EnVision system (DAKO, Denmark), and DAB (diaminobenzidine) as the chromogen (Sigma, ST Louis, USA). Mounted slides were examined by light microscopy and immunoreactivity was assessed using a 3-grade system, in which 0 denoted absence of staining; 1 denoted minimal staining; and 2 denoted uniform and intense staining. Only specimens with grade 2 immunoreactivity were considered positive.

3. Cell Culture

HCC HepG2 cell line was obtained from the American Type Culture Collection (HB-8065, ATCC, Rockville, Md., USA). Cells were maintained in Eagle's Minimum Essential Media (MEM) supplemented with 10% of fetal bovine serum (FBS), 100 U/ml of penicillin, and 100 mg/ml of streptomycin (all reagent from ATCC) at 37° C. in a 5% $CO_2$ incubator.

4. Retroviral Transduction of shRNAs

ShRNA (short hairpin RNA) sequence specified by shOligos were inserted into the pSuper.puro expression vector according to the manufacturer's instructions (OligoEngine, Seattle, Wash.) (32). We prepared two shOligos each for the Notch3 and Notch1 receptors to rule out the possibility of off-target shRNA effects. The two pairs of targeted sequences in Notch3 and Notch1 were as follows: Notch3 (#1); 5'-ctcccctcaccacctaataaa-3' (SEQ ID NO: 1); Notch3 (#2): 5'-gggggacctgccgccgtggctata-3' (SEQ ID NO: 2); Notch1 (#1): 5'-ggccgtcatctccgacttca-3' (SEQ ID NO: 3); Notch1 (#2): 5'-gcctcttcgacggctttga-3' (SEQ ID NO: 4). For a negative control, we prepared a population of HepG2 cells harboring a pSuper.puro provirus expressing a GL2 luciferase specific shRNA (33).

Retroviruses were produced by transfecting pSuper.puro expression vectors into Phoenix A packaging cells (kindly provided by Dr. Gary Nolan) using the calcium phosphate precipitation method (34).

Viral supernatants were collected at 48 h and 72 h post transfection, pooled, filtered (pore size 0.45 µm) and stored at −80° C.

The day prior to infection 50-70,000 HepG2 cells were seeded per well of 6-well plates To achieve efficient retroviral transduction, undiluted viruses were applied to cells by spinoculation (centrifugation at 2200 RPM for 45 minutes at 32° C.) in the presence of 8 µg/ml Polybrene (Sigma) followed by an additional 5 hr of incubation at 32° C. Viral supernatants were subsequently replaced by fresh complete medium and cells were allowed to recover for 48 hours at 37° C. Stably infected populations of cells were selected in growth media supplement with 1.8 µg/ml puromycin. Puromycin resistance was routinely achieved after 4 days of selection with two changes of media.

5. Transfection of Small Interfering RNA

Twenty four hours prior to transfection both Notch3 shRNA and GL2 infected cells were seeded into 6 well plates in antibiotic free MEM. HepG2 cells grown to a confluence of 40% were transfected with 40 nM of validated p53 siRNA and scrambled RNA (scRNA) (Invitrogen). Immediately before transfection the culture medium was removed and the transfection was performed using Lipofectamine2000 and Opti-MEM media (invitogen) according to the manufacturers recommendations. Five hours post transfection the medium was replaced with fresh serum containing medium. Transfection efficiency was above 90% as determined by transfection with a fluorescein-labelled siRNA (Invitrogen). Cells were collected at 48 h and 72 h post-transfection for examining the expression of p53 protein by Western blot or subjected to doxorubicin treatment for 24 h. Cell viability was subsequently assessed by trypan blue staining.

Two siRNA sequences for silencing human HES1 were synthesized in duplex, HES1 inhibition was assessed after transient transfection of HepG2 cells with 40 nM of each siRNA for 72 hours.

6. Doxorubicin Treatments

Stably infected cell populations of HepG2 cells were seeded into 6-well dishes and allowed to attach for 24 hours, washed and cultured in fresh complete medium with 100 ug/ml doxorubicin (Sigma) for 1 h, 3 h, 6 h, 12 h, 18 h and 24 h. Doxorubicin incorporation was detected by FACS counting of 10,000 events.

7. Cell Death and Cytotoxicity Assays

Subsequent to doxorubicin treatment attached and floating HepG2 cells were collected in culture medium, pelleted by centrifugation and the degree of cell death was evaluated by trypan blue staining. Cellular necrosis was assessed by the standard, clinical LDH (lactate dehydrogenase) release assay performed with the culture medium of untreated and doxorubicin treated cells.

8. RNA Analysis

Total cellular RNAs were prepared with by Triazol (Invitrogen, Paisley, Scotland) according to the manufacturer's instructions. Four micrograms of total RNA were treated with DNAse I (Invitrogen) to eliminate contaminating genomic DNA. Reverse transcription (RT) into cDNAs was performed in a 30 μl reaction including: 1× RT buffer, 0.4 mM dNTPs, 5 mM dithiothreitol (DTT), 0.5 μM oligodT, 3 μM random primers, 240U Superscript II (all reagents from Invitrogen.). The RT reaction was carried out at 42° C. for 1 h, followed by 5 min at 95° C. to inactivate the enzyme. The relative expression of the P53, WAF1, Notch1, HES1 and β-actin genes was determined by semi-quantitative end-point PCR amplification. PCR products were resolved on 2% agarose gels stained with ethidium bromide and analyzed by fluorometric analysis (Quantity one, Biorad, CA, USA). PCR primers were as follows: WAF1 (FW 5'-aagaccatgtggacctgtca-3' and REV 5'-ggcttcctcttgga-gaagat-3', SEQ ID NOS: 5 and 6, respectively); P53 (FW 5'-gacccaggtccagatgaagct-3' and REV 5'-accgtagctgccctgg-taggt-3', SEQ ID NOS: 7 and 8, respectively); HES1 (FW 5'-gctggtgctgtctggatg-3' and REV 5'-cattcctgctctcgccttc-3', SEQ ID NOS: 9 and 10, respectively).

9. Protein Analysis

Cultured cells were dissolved in lysis buffer containing 10 mM Tris-HCl pH 7.4, 2.5 mM MgCl2, 1% TritonX 100, 1 mM DTT, 0.1 mM phenylmethylsulfonyl fluoride (PMSF), 1 mM $Na_3VO_4$, 1 mM NaF and protease inhibitors (Sigma Chemical Company, St. Louis, Mo.). The lysate was centrifuged at 4° C., 15,000×g, for 15 min and the supernatant assayed for protein concentration by Bio-Rad protein assay (Bio-Rad). Proteins were boiled at 95° C. for 10 min in 1×SDS (sodium dodecil sulfate) loading buffer (65 mM Tris-HCl, Ph 7.5, 65 mM 2-mercaptoethanol, 1% SDS, 10% glycerol and 0.003% bromophenol blue), resolved by poly-acrilamide gels and blotted on nitrocellulose membranes (Hybond C Extra, Amersham Pharmacia, Little Chalfont, UK). Membranes were stained with Red Ponceau solution (Sigma), blocked in 5% non-fat dry milk for 50 min in PBS and then incubated with appropriate primary antibody. Primaries antibodies and dilutions were as follows: anti-Notch3 polyclonal antibody (sc-5593, Santa Cruz Biotechnology) 1:300, anti-Gadd45α polyclonal antibody (AB3863, Chemicon International, Temecula, Calif.) 1:1000, Anti-p21 monoclonal antibody (Clone SX118, Dako) 1:100, anti p53 monoclonal antibody (Clone DO-7, Dako) 1:500, anti-Kip1/p27 monoclonal antibody (Clone 57, BD Biosciences, San Jose, Calif.) 1:2300, Cleaved PARP monoclonal antibody (9546, Cell Signaling Technology, Beverly, Mass.) 1:200, anti p-p53 polyclonal antibody (sc-18079-R, Santa Cruz Biotechnology) 1:300, anti Notch1 polyclonal antibody 1:200 and anti β-actin monoclonal antibody (Clone AC-40, Sigma) 1:1000.

After repeated washing in PBS containing 0.1% Tween 20 (PBST), membranes were incubated with anti-mouse or anti-rabbit HRP-conjugated secondary antibodies using the EnVision dextran polymer visualization system (Dako). Membranes were washed and autoradiographs were obtained by chemiluminescence reaction (ECL reagents, Amersham). Digital images of autoradiographs were acquired with a Fluor-S MultiImager scanner (BioRad) and signals were quantitated with Quantity-one densitometric software (BioRad, Hercules, Calif.) in absorbance units after light calibration with a reference autoradiograph.

10. Comet Assay

DNA strand-breaks were quantified by the alkaline comet assay. Briefly, at different time points after exposure to doxorubicin, $10^5$ cells were embedded in 0.7% low melting-point agarose and transferred onto agarose covered microscope slides. Subsequently, slides were incubated for 1 h at 4° C. in fresh lysis buffer (2.5 M NaCl, 100 mM $Na_2$ EDTA, 10 mM Tris-HCl, 1% Triton X-100, pH 10.0). Slides were than placed on a horizontal gel electrophoretic chamber filled with cold alkaline unwinding/electrophoresis solution (300 mM NaOH, 1 mM $Na_2$ EDTA, pH 13.0) for 25 min. After electrophoresis (25 V, 300 mA for 25 min), slides were washed with 0.4 M Tris (pH 7.5), dried in absolute ethanol for 2 min and stained with ethidium bromide. Comets were analyzed with a fluorescence microscope (Nikon, USA) and quantitated by determination of the 'tail moment' ($^{TM}$) with CASP Software. Fifty cells were analyzed per measurement to calculate the mean values.

11. Statistical Analysis

Data were analyzed using the statistical function of Stat-View 5.0 (SAS Institute Inc, Cary N.C.). Results were presented as mean+standard error (S.E.) of data originating from two independent experiments. Statistical significance of the results was evaluated using Student's t-test. P values less then 0.05 were considered statistically significant.

12. Assessment of Notch3 Protein Expression

Figure 1:
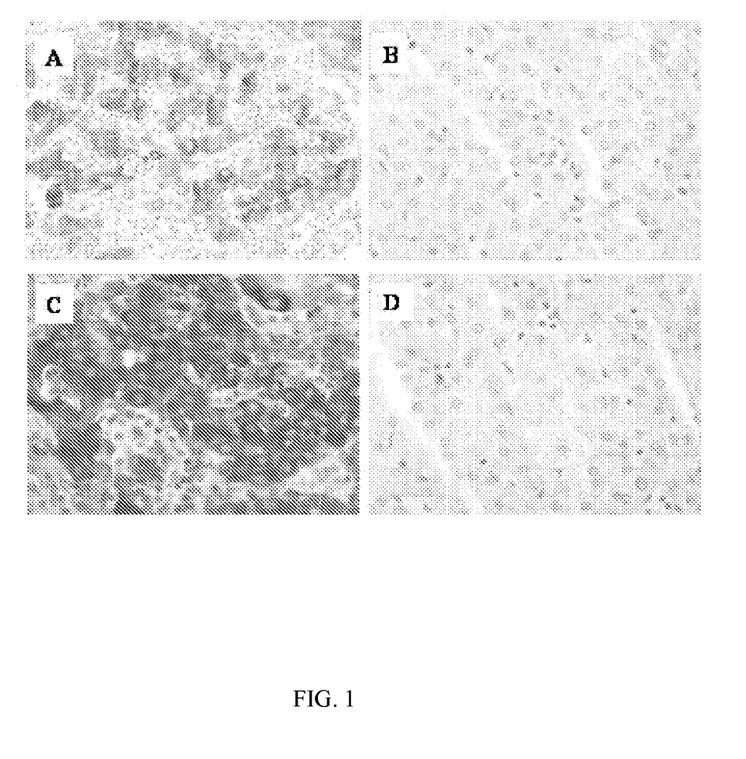

The expression of the Notch1, 3 and 4 receptors has been assessed by immunohistochemistry in 20 paired samples of HCC and surrounding tissues. Normal liver and chronic hepatitis samples did not express either of these three Notch receptors. There was no significant differences between CE and HCC liver specimens for Notch1 and Notch4 immuno-reactivity. However, Notch3 positive expression was found in neoplastic hepatocytes in 15 of 20 HCC (75%) whereas CE specimens were considered negative in all cases since Notch3 detection was occasionally seen in isolated hepatocytes (FIG. 1) No association was found among tumor grading, virus infection and Notch3 expression even though the majority of the analyzed cases were high grade tumors.

This assessment provides the first in vivo evidence that up-regulated Notch3 expression is specifically correlated with hepatocyte neoplasia; and also reveal that at least in comparison to Notch1 and 4, Notch3 could be selectively involved in HCC survival signaling and/or progression.

13. Depletion of Notch3 in HepG2 Cells

Effects on Specific Regulatory Factors

Figure 2:
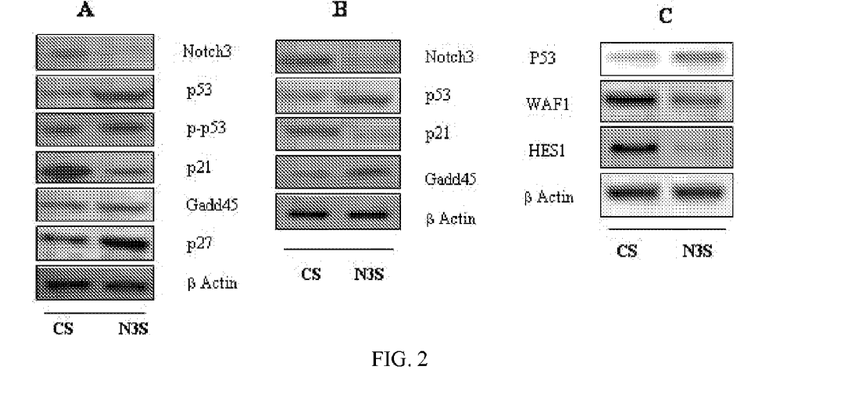

Notch3 expression has been ablated with Notch3 specific shRNAs in HepG2 cells by stable retroviral transduction and examined the concomitant effects on cellular growth and doxorubicin sensitivity. Notch3 protein levels were highly reduced in HepG2 cells by two different Notch3 specific shRNA retroviruses in comparison to an irrelevant GL2 luciferase specific shRNA control virus (see Western blot in FIG. 2A). Both Notch3 shRNAs produced equally penetrant Notch3 knock-downs (FIG. 2A-B).

Notch 3 knock-down differentially affected the levels of specific cellular proteins associated with cellular proliferation, DNA repair and apoptosis. As shown in FIG. 2A, the endogenous levels of p27 and GADD45α, P53 and activated p-P53 were elevated from 2 to 5 fold after Notch3 depletion, while p21 protein levels were reduced 4 fold. RNA analysis presented in FIG. 2C revealed comparable results for p53 and p21 gene transcription. In addition the expression of HES1, a direct target of the Notch intracellular domain (NICD), was also diminished by the Notch3 knock-down.

14. Notch3 Knock-Down Effects in Doxorubicin Treated HepG2 Cells

Figure 4:
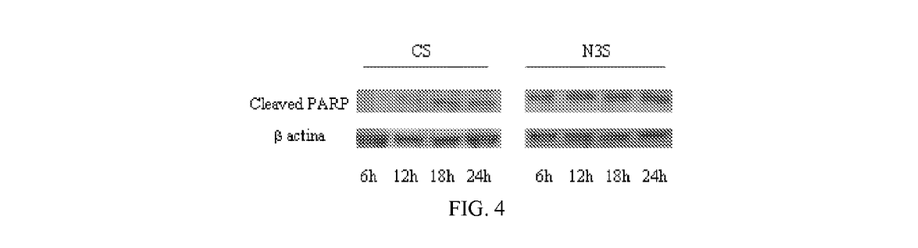

It has been investigated whether Notch3 confers resistance to doxorubicin induced cell death of HepG2 liver carcinoma cells. Infection with either Notch3 shRNA did not alter HepG2 growth rates, which were assessed one week post-infection by propidium iodide staining and flow cytometry (data not shown). However, the mortality of HepG2 cells stably expressing Notch3 shRNAs (in comparison to a luciferase shRNA negative control) doubled and tripled in response to doxorubicin treatments of 6 and 24 hours respectively, as revealed by trypan blue dye exclusion (FIG. 3). Doxorubicin treatment also caused cleavage of PARP. PARP is a 115 kDa nuclear protein involved in DNA repair, which is one of the earliest proteins cleaved in apoptotic responses. After 6 h of doxorubicin treatment, a clear increase in the accumulation of PARP's apoptosis specific 89 kDa cleavage fragment was observed in the Notch3 depleted cells. (FIG. 4).

Figure 5:
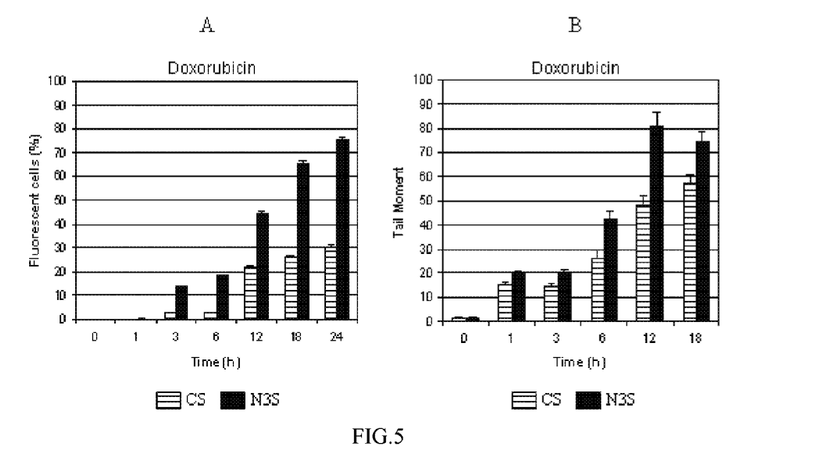

Comet assay has been largely used to measure DNA damage in response to different DNA-damaging agents. In this assay cleaved DNA migrates from the nucleus forming a comet that is visualized as a cell with a round head and tail. Basal DNA damage measured by the comet assay showed that GL2 control cells had the same endogenous degree of DNA damage as Notch3 depleted cells (P=0.6686). A time course analysis was performed to examine the DNA strand breaks induced by doxorubicin in both GL2 control and Notch3 deficient cells. This analysis revealed a time-dependent increase in the "TM" values obtained with significantly higher levels of DNA damage in Notch3 depleted cells (FIG. 5A). After 24 h of treatment with doxorubicin Notch3 depleted cells were so severely damaged that it was no longer possible to quantitate the degree of DNA fragmentation. FACS analysis also revealed that Notch3 depleted cells took up and/or retained higher levels of doxorubicin than GL2 negative control cells with a significant difference in doxorubicin uptake after only 3 h of doxorubicin treatment (FIG. 5B).

15. Notch1 Depletion in Doxorubicin Treated HepG2 Cells

Since different studies demonstrated that high p21 levels protect human cancer cells from apoptosis during chemotherapy and radiotherapy treatments, we investigated if p21, which was down-regulated in Notch3 depleted cells, was involved in the sensitivity of HepG2 cells to doxorubicin. A previous study of HCC cell lines showed that Notch1 over-expression inhibits cellular growth through p21 up regulation. Consistent with this observation, it has been found that loss of Notch1 expression by targeted shRNA knock-down greatly reduced p21 protein expression by immunoblot analysis (FIG. 6). However, the inhibitory effect of Notch1 KD on p21 expression was independent of P53 and p-P53 expression, because their levels were unaffected by Notch1 depletion (FIG. 6). Importantly, unlike Notch3 ablation the loss of Notch1 failed to sensitize HepG2 cells to doxorubicin-mediated cell death (FIG. 10). Thus our findings in HepG2 cells do not support a role for p21 in their sensitivity to doxorubicin dependent apoptosis.

16. Ablation of P53 in Notch3 Depleted Cells Doxorubicin Treated

Figure 7:
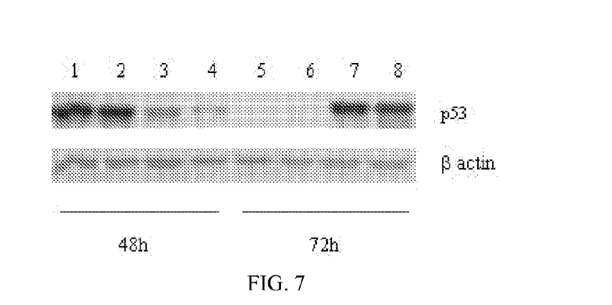

P53 expression was ablated in the Notch3 knock-down cells, to determine the significance of P53 up-regulation for the enhanced apoptotic response of Notch3 depleted cells to doxorubicin treatment. Endogenous P53 expression was ablated in Notch3 KD and GL2 control HepG2 cells by efficient cationic lipid mediated transfection of a cocktail of p53 specific siRNAs in comparison to a scrambled mixture of unrelated siRNAs (scRNAs). Western blotting revealed that P53 protein levels were dramatically reduced at 48 hr and undetectable by 72 h post-transfection respectively with P53 specific siRNAs in comparison to the scRNA negative control (FIG. 7).

Figure 8:
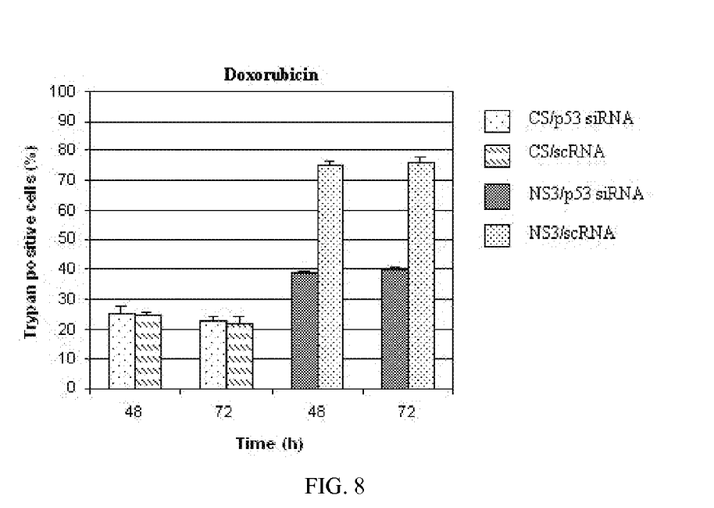
Figure 9:
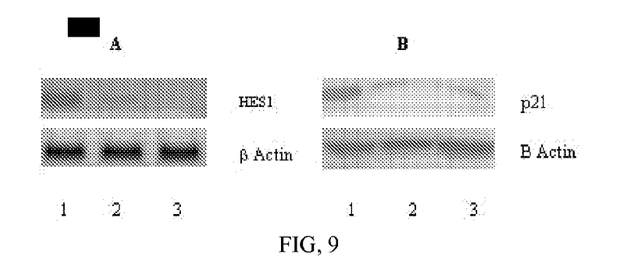

Transfected cells were treated with 100 μg/ml doxorubicin for 24 h. Interestingly down-regulation of P53 specifically removed most of the enhanced apoptotic reaction of the Notch3 depleted cells. As shown in FIG. 8, after doxorubicin treatment cell viability was 40% in Notch3 depleted cells transfected with p53 siRNA compared with 75% in Notch3 depleted cells transfected with scRNA. However, P53 depletion did not affect the sensitivity of GL2 infected cells to doxorubicin (FIG. 8), thus indicating that endogenous Notch3 prevents the ability of endogenous P53 to amplify the death promoting effects of doxorubicin.

The invention claimed is:

1. A method of treating Hepatocellular Carcinoma (HCC), the method comprising: administering a pharmaceutical composition comprised of a Notch3 inhibitor, one or more anti-tumoral chemotherapeutic agents causing cellular apoptosis or acting on cellular proliferation, and a pharmaceutically acceptable carrier to a patient in need thereof, in one or more therapeutically effective doses.

2. A method of treating Hepatocellular Carcinoma (HCC) using a pharmaceutical kit comprising (i) a first vial comprised of a Notch3 inhibitor and a pharmaceutical acceptable carrier, (ii) a second vial comprised of one or more anti-tumoral chemotherapeutic agents causing cellular apoptosis or acting on cellular proliferation, and a pharmaceutical acceptable carrier, and (iii) optional additional vials, each one comprised of an antitumoral chemotherapeutic agent and a pharmaceutical acceptable carrier, the method comprising: co-administering the first and the second vials or the first and the optional additional vials of the pharmaceutical kit to a patient in need thereof, in one or more therapeutically effective doses.

3. The method according to claim 1, wherein said one or more anti-tumoral chemotherapeutic agents is or are selected from the group consisting of doxorubicin, 5 fluorouracil, paclitaxel, irinotecan, patupilone, everolimus, multikinase inhibitors, and epidermal growth factor receptor (EGFR) inhibitors.

4. The method according to claim 1, wherein said one or more anti-tumoral chemotherapeutic agents is or are comprised of doxorubicin.

5. The method according to claim 1, wherein said Notch 3 inhibitor is selected from the group consisting of siRNAs complementary to the mRNA coding for Notch3, shRNAs complementary to the mRNA coding for Notch3, synthetic oligonucleotides complementary to the mRNA coding for Notch3, anti-Notch3 antibodies, and Notch3 antagonists.

6. The method according to claim 5, wherein said Notch3 inhibitor is an siRNA or shRNA inserted in a viral vector comprising a tumor specific promoter or liver specific target promoter.

7. The method according to claim 5, wherein said Notch3 inhibitor is a synthetic oligonucleotide inserted into a lipoplex.

8. The method according to claim 2, wherein said one or more anti-tumoral chemotherapeutic agents is or are selected from the group consisting of doxorubicin, 5 fluorouracil, paclitaxel, irinotecan, patupilone, everolimus, multikinase inhibitors, and epidermal growth factor receptor (EGFR) inhibitors.

9. The method according to claim 2, wherein said one or more anti-tumoral chemotherapeutic agents is or are comprised of doxorubicin.

10. The method according to claim 2, wherein said Notch 3 inhibitor is selected from the group consisting of siRNAs complementary to the mRNA coding for Notch3, shRNAs complementary to the mRNA coding for Notch3, synthetic oligonucleotides complementary to the mRNA coding for Notch3, anti-Notch3 antibodies, and Notch3 antagonists.

11. The method according to claim 10, wherein said Notch3 inhibitor is an siRNA or shRNA inserted in a viral vector comprising a tumor specific promoter or liver specific target promoter.

12. The method according to claim 10, wherein said Notch3 inhibitor is a synthetic oligonucleotide inserted into a lipoplex.

13. The method according to claim 1, wherein said one or more anti-tumoral chemotherapeutic agents is or are comprised of a multikinase inhibitor selected from the group consisting of sorafenib and sunitinib.

14. The method according to claim 1, wherein said one or more anti-tumoral chemotherapeutic agents is or are comprised of an EGFR inhibitor selected from the group consisting of cetuximab, erlotinib, gefitinb, brivanib, and lapatinib.

15. The method according to claim 2, wherein said one or more anti-tumoral chemotherapeutic agents is or are comprised of a multikinase inhibitor selected from the group consisting of sorafenib and sunitinib.

16. The method according to claim 2, wherein said one or more anti-tumoral chemotherapeutic agents is or are comprised of an EGFR inhibitor selected from the group consisting of cetuximab, erlotinib, gefitinb, brivanib, and lapatinib.

17. The method according to claim 1, wherein at least one anti-tumoral chemotherapeutic agent is sorafenib.

18. The method according to claim 17, wherein at least one anti-tumoral chemotherapeutic agent is sorafenib.

19. The method according to claim 1, wherein at least one anti-tumoral chemotherapeutic agent is sorafenib.

20. The method according to claim 17, wherein at least one anti-tumoral chemotherapeutic agent is sorafenib.

* * * * *